US009527657B2

(12) United States Patent
Anderson et al.

(10) Patent No.: US 9,527,657 B2
(45) Date of Patent: Dec. 27, 2016

(54) DISPENSING VALVES

(71) Applicant: Consort Medical PLC, Hemel Hempstead Hertfordshire (GB)

(72) Inventors: Ian Anderson, Cambridgeshire (GB); Alastair Willoughby, Cambridgeshire (GB); Joshua Stroobant, Cambridgeshire (GB); Richard Warby, Cambridgeshire (GB); Paul Allsop, Norfolk (GB)

(73) Assignee: CONSORT MEDICAL PLC, Hemel Hempstead, Hertfordshire (GB)

( * ) Notice: Subject to any disclaimer, the term of this patent is extended or adjusted under 35 U.S.C. 154(b) by 0 days.

(21) Appl. No.: 14/406,083

(22) PCT Filed: Jun. 7, 2013

(86) PCT No.: PCT/GB2013/051505
§ 371 (c)(1),
(2) Date: Dec. 5, 2014

(87) PCT Pub. No.: WO2013/182856
PCT Pub. Date: Dec. 12, 2013

(65) Prior Publication Data
US 2015/0183571 A1    Jul. 2, 2015

(30) Foreign Application Priority Data

Jun. 7, 2012 (GB) .................................. 1210082.2

(51) Int. Cl.
*B65D 83/00* (2006.01)
*B65D 83/24* (2006.01)
(Continued)

(52) U.S. Cl.
CPC .............. *B65D 83/24* (2013.01); *A61M 5/142* (2013.01); *A61M 5/14526* (2013.01);
(Continued)

(58) Field of Classification Search
CPC ....... B65D 83/24; B65D 83/48; B65B 31/043; A61M 5/155
(Continued)

(56) References Cited

U.S. PATENT DOCUMENTS 2,506,722 A * 5/1950 Kuehn ................... F16K 21/14
251/322
3,257,035 A * 6/1966 Dovaston ............... A62C 13/64
169/89

(Continued)

FOREIGN PATENT DOCUMENTS

CN          101195054        6/2008
CN          201410196        2/2010

OTHER PUBLICATIONS

Office Action for Chinese Patent Family member No. CN201380029780.6 dated Jul. 24, 2015 (in Chinese with English Translation) (18 pages).

(Continued)

*Primary Examiner* — Patrick M Buechner
*Assistant Examiner* — Jeremy W Carroll
(74) *Attorney, Agent, or Firm* — Smith, Gambrell & Russell, LLP

(57) ABSTRACT

A valve for discharging a fluid, comprising:
 a valve body at least partially defining a fluid chamber; and
 a valve stem extending into the fluid chamber, the valve stem comprising an outlet port for transfer, in use, of fluid from the fluid chamber into the valve stem;
 the valve stem being slidably movable relative to the valve body from:
 i) a non-dispensing position in which the outlet port is out of communication with the fluid chamber; to
(Continued)

ii) a dispensing position in which the outlet port is in fluid communication with the fluid chamber so as to permit transfer of the fluid from the fluid chamber into the valve stem;

wherein the valve further comprises a locking member which is configured to prevent return of the valve stem into the non-dispensing position once the valve stem slides beyond a locking position.

54 Claims, 11 Drawing Sheets

(51) Int. Cl.
    *B65B 51/26*     (2006.01)
    *B65B 51/30*     (2006.01)
    *B65B 31/04*     (2006.01)
    *A61M 5/20*     (2006.01)
    *A61M 5/155*     (2006.01)
    *A61M 39/22*     (2006.01)
    *A61M 5/168*     (2006.01)
    *A61M 5/44*     (2006.01)
    *B65D 83/48*     (2006.01)
    *A61M 5/142*     (2006.01)
    *A61M 5/145*     (2006.01)

(52) U.S. Cl.
CPC ........ *A61M 5/155* (2013.01); *A61M 5/16804* (2013.01); *A61M 5/2053* (2013.01); *A61M 5/44* (2013.01); *A61M 39/22* (2013.01); *B65B 31/045* (2013.01); *B65B 51/26* (2013.01); *B65B 51/30* (2013.01); *B65D 83/48* (2013.01); *A61M 2005/14513* (2013.01); *A61M 2207/00* (2013.01); *A61M 2207/10* (2013.01); *Y10T 29/49* (2015.01); *Y10T 29/49808* (2015.01)

(58) Field of Classification Search
USPC ............. 222/402.12, 402.14, 153.12, 153.04
See application file for complete search history.

(56) References Cited

U.S. PATENT DOCUMENTS

| | | | | |
|---|---|---|---|---|
| 3,305,144 | A * | 2/1967 | Beres | B65D 83/207 222/402.13 |
| 3,395,838 | A * | 8/1968 | Beres | B65D 83/207 222/402.14 |
| 3,729,120 | A * | 4/1973 | Sette | B65D 83/205 222/153.11 |
| 4,243,161 | A * | 1/1981 | Ewald | B65D 83/205 222/402.14 |
| 4,260,080 | A * | 4/1981 | Gailitis | B65D 83/24 222/402.14 |
| 4,428,509 | A * | 1/1984 | Emerson | B65D 83/205 222/153.02 |
| 4,941,600 | A * | 7/1990 | Berriochoa | B65D 83/205 222/402.13 |
| 5,228,646 | A * | 7/1993 | Raines | A61M 39/22 251/322 |
| 2002/0020722 | A1* | 2/2002 | Uemura | B65D 83/206 222/402.13 |
| 2007/0007479 | A1 | 1/2007 | Efinger et al. | |
| 2014/0114248 | A1 | 4/2014 | DeSalvo et al. | |

OTHER PUBLICATIONS

International Preliminary Report on Patentability of PCT/GB2013/051505 dated Dec. 9, 2014. 6 Pages.
Written Opinion of the International Searching Authority for PCT/GB2013/051505 dated Dec. 7, 2014. 5 Pages.
International Search Report for PCT/GB2013/051505 dated Aug. 26, 2013. 3 Pages.

* cited by examiner

DISPENSING VALVES

FIELD

The present disclosure relates to improvements in or relating to dispensing valves. In particular, it relates to a valve which comprises a locking member which is configured to prevent return of the valve into a non-dispensing configuration once the valve has been actuated. A method of using such a valve is also described. Methods and apparatus for filling such a valve are further described.

BACKGROUND

Valves for discharging a fluid, such as a volatile propellant are known in the art. Such valves may be metered valves, which are designed to dispense a pre-determined volume of fluid on each actuation of the valve, or continuous flow valves which are designed to discharge fluid for as long as the valve is held in a discharging configuration and the fluid supply is not exhausted. An example of the latter, continuous flow valve may be found on a typical aerosol container of the type used for dispensing deodorant. In such an aerosol container, a valve stem of the continuous flow valve is depressed relative to a valve body by manual displacement of an actuator button connected to the valve stem. This movement of the valve stem relative to the valve body opens an exit path from the interior of the valve to allow discharge of fluid due to the boiling off of the volatile propellant contained within the aerosol container. Such aerosol containers are typically relatively large and are designed to be actuated a number of times before the contents of the aerosol container are exhausted.

SUMMARY OF THE DISCLOSURE

Against this background there is provided in a first aspect, a valve for discharging a fluid, comprising:

a valve body at least partially defining a fluid chamber; and a valve stem extending into the fluid chamber, the valve stem comprising an outlet port for transfer, in use, of fluid from the fluid chamber into the valve stem;

the valve stem being slidably movable relative to the valve body from:

i) a non-dispensing position in which the outlet port is out of communication with the fluid chamber; to ii) a dispensing position in which the outlet port is in fluid communication with the fluid chamber so as to permit transfer of the fluid from the fluid chamber into the valve stem;

wherein the valve further comprises a locking member which is configured to prevent return of the valve stem into the non-dispensing position once the valve stem slides beyond a locking position.

Advantageously, the valve of the present invention is configured to ensure that once the valve stem is moved into the dispensing position, in order to actuate the valve and to start to discharge the fluid, the valve remains in the dispensing position to ensure that fluid continues to be discharged until the supply of fluid is exhausted. Whilst the valve may be used where a relatively large quantity of fluid is to be dispensed, it finds particular application in where a relatively small quantity of fluid is to be dispensed, for example a volume of from 10 to 500 microlitres.

The valve may be a single-discharge valve which is configured only to discharge a single quantum of fluid in a single discharge operation during its useful life.

The valve of the present disclosure finds particular application when used as a disposable valve which is configured to be used only once before being disposed of or recycled. The valve provides a compact, simple means for discharging a single quantum of fluid.

The locking member may be located within the valve body. By providing the locking member within the valve body a more compact valve may be achieved.

Alternatively, the locking member may be formed as a part of the valve body or may be located outside the valve body.

The locking member and the valve stem may comprise inter-engaging members, wherein the inter-engaging members may:

a) contact one another during movement of the valve stem towards the dispensing position and permit movement of the valve stem into the dispensing position; and b) contact one another during attempted movement of the valve stem from beyond the locking position back towards the dispensing position and prevent movement of the valve stem back into the non-dispensing position.

The inter-engaging members may contact one another during movement of the valve stem towards the dispensing position and may permit movement of the valve stem into the dispensing position by flexing or other distortion of at least one of the inter-engaging members.

In one example, the inter-engaging member of the valve stem may comprise a flange. A distal edge of the flange may be angled to promote flexing of the locking member during movement of the valve stem into the dispensing position.

Advantageously, the flange of the valve stem which serve as one of the inter-engaging members may also provide a seat for a biasing member of the valve.

The inter-engaging member of the locking member may comprise at least one flexible latch.

At least one flexible latch may exhibit elastic behaviour.

The locking member may comprise four or more flexible latches.

The locking member may comprise an annular ring and the four flexible latches may be equi-spaced about the annular ring.

The locking position of the valve stem may be defined as a point where the inter-engaging member of the valve stem slides beyond, and disengages from, the inter-engaging member of the locking member.

The valve may further comprise a biasing member for biasing the valve stem into the non-dispensing position.

The biasing member may be a compression spring located in the valve body and extending between the valve body and the valve stem.

The valve may further comprise a seal member sealing between the valve body and the valve stem.

The valve body may comprise a cup-shaped portion having an open mouth through which extends the valve stem; wherein the open mouth may be closed by the seal member.

The valve may further comprise a crimped ferrule for retaining the seal member is sealing engagement with the valve body and valve stem.

The valve may comprise only a single seal member in the form of the seal member which functions as both a dynamic seal with the valve stem and a static seal with the valve body. Advantageously, the valve design may only require one sealing member in the form of the seal member. This may help to reduce the cost of the valve and also to reduce the danger of leakage of fluid during storage since the surface area of the sealing material exposed to the fluid may be reduced compared to a valve containing multiple different sealing members.

The fluid chamber may be closed by the valve body and the seal member such that, in use, a quantum of fluid is sealed within the fluid chamber. Advantageously, the valve may be configured to contain the quantum of fluid, such as volatile propellant, wholly within the valve itself in a chamber defined by the combination of the valve body and the seal member. This allows for an extremely compact valve and removes the need for any separate storage container for containing the volatile propellant.

Prior to movement of the valve stem beyond the locking position, the valve stem may be slidably movable relative to the valve body into:

iii) a filling position in which the outlet port is in fluid communication with the fluid chamber to allow pressure-filling of the fluid chamber via the valve stem and outlet port.

Advantageously, pressure-filling of the valve may be achieved without causing the valve stem to become locked.

An external portion of the valve stem may comprise a connector for releasably connecting the valve stem to a pressure-filling apparatus. The connector may be a groove in the valve stem. Alternatively, the connector may be a flange on the valve stem.

The valve stem may comprise a tapered distal end.

The present disclosure provides in another aspect, a method of discharging a fluid from a valve of the type comprising:

a valve body at least partially defining a fluid chamber containing a fluid; and a valve stem extending into the fluid chamber, the valve stem comprising an outlet port;

the method comprising the steps of:

i) starting with the valve stem a non-dispensing position in which the outlet port is out of communication with the fluid chamber;

ii) moving the valve stem by a sliding stroke relative to the valve body into a dispensing position in which the outlet port is in fluid communication with the fluid chamber to thereby transfer the fluid from the fluid chamber into the valve stem via the outlet port;

iii) discharging the fluid from an external open end of the valve stem;

wherein during the sliding stroke of step ii) the valve stem is locked by being moved beyond a locking position such that return of the valve stem into the non-dispensing position is prevented and the valve stem is maintained in the discharging position to thereby ensure that the fluid contained in the fluid chamber is fully discharged.

The valve may only discharge a single quantum of fluid in a single discharge operation during its useful life.

Return of the valve stem into the non-dispensing position from beyond the locking position may be prevented by inter-engagement between the valve stem and a locking member.

The inter-engagement between the valve stem and the locking member:

a) may produce contact therebetween during movement of the valve stem towards the dispensing position and permits movement of the valve stem into the dispensing position; and b) may produce contact therebetween during attempted movement of the valve stem from beyond the locking position back towards the dispensing position and prevents movement of the valve stem back into the non-dispensing position.

The valve stem and/or the locking member may flex or otherwise distort as the valve stem moves beyond the locking position.

The valve stem and/or the locking member may flex or otherwise distort elastically as the valve stem moves beyond the locking position.

The valve stem may become locked at a point where a flange of the valve stem slides beyond, and disengages from, the locking member.

The valve stem may be biased into the non-dispensing position.

The fluid chamber may be closed by the valve body and a seal member such that, in use, a quantum of fluid is sealed within the fluid chamber.

The fluid may comprise a volatile propellant.

Prior to movement of the valve stem beyond the locking position, the valve stem may be slidably movable relative to the valve body into:

iii) a filling position in which the outlet port is in fluid communication with the fluid chamber to allow pressure-filling of the fluid chamber via the valve stem and outlet port.

The present disclosure provides in another aspect, use of a valve which can only discharge a single quantum of volatile propellant fluid in a single discharge operation during its useful life, to power actuation of a medicament dispenser.

The valve of the present disclosure finds particular application when used as part of a medicament dispenser which is configured to be used only once before being disposed of or recycled. The valve provides a compact, simple means for discharging a single quantum of fluid that can be used as part of a means for actuating the medicament dispenser. The medicament dispenser may be a syringe, an ophthalmic delivery device, a nasal system, an oral inhaler, or a transdermal delivery device.

The valve may be of the type comprising:

a valve body at least partially defining a propellant fluid chamber containing the propellant fluid; and a valve stem extending into the propellant fluid chamber.

The present disclosure provides in another aspect, a syringe comprising:

a barrel having an outlet at a front end; and a stopper axially movable in the barrel; the syringe further comprising a valve as described above.

The valve may in the non-dispensing position comprise a volatile propellant within the fluid chamber, wherein the syringe may be actuated to move the stopper in the barrel by moving the valve stem into the dispensing position.

The stopper may define and separate a first chamber and a second chamber, the first chamber being axially forwards of the stopper and being configured for containing a medicament, and the second chamber being axially rearwards for the stopper and being configured to receive propellant from an outlet of the valve stem.

The valve may be coupled to a rear end of the barrel of the syringe.

The syringe may further comprise a manually movable actuator for actuating the valve. The manually movable actuator may be a button or flexible membrane coupled to the valve body of the valve.

Use of the valve described above as part of a syringe allows for a very compact and reliable power source for moving the stopper in the barrel of the syringe by use of the energy available from boiling off of the volatile propellant.

In accordance with the present disclosure, by ensuring that the valve is configured to remain open once actuated, such that the fluid intended to be discharged is fully discharged, reliable operation of the syringe is made more likely. For example, the design of the valve removes the possibility of a partial actuation, or re-closing, of a valve which might therefore not discharge a sufficient volume of propellant into the barrel to fully move the stopper as required to dispense medicament or other product contained within the syringe.

The valve finds particular application when used with a syringe which is itself intended only to be used once and then disposed of.

The present disclosure provides in another aspect, a method of pressure-filling a valve of the type comprising:

a valve body at least partially defining a fluid chamber;

a valve stem extending into the fluid chamber, the valve stem comprising an outlet port;

a seal member sealing between the valve body and the valve stem; and a ferrule for retaining the seal member and valve stein to the valve body;

wherein an external portion of the valve stem comprises a connector;

the method comprising the steps of:

i) starting with the valve stem a non-dispensing position in which the outlet port is out of communication with the fluid chamber;

ii) engaging a pressure-filling apparatus with the connector of the valve stem;

iii) moving the valve stem into a filling position, by operation of the pressure-filling apparatus, such that the valve stem slides relative to the valve body until the pressure-filling apparatus contacts the ferrule iv) pressure-filling the fluid chamber and/or valve body; and v) moving the valve stem, by operation of the pressure-filling apparatus, back into the non-dispensing position;

wherein the distance between the connector and the ferrule in the non-dispensing position of the valve is configured such that in the filling position, with the pressure-filling apparatus in contact with the ferrule, the outlet port of the valve stem is in fluid communication with the fluid chamber to permit transfer of fluid into the fluid chamber.

The valve may further comprise a locking member such that the valve stem may be locked in a dispensing position by being moved beyond a locking position such that return of the valve stem into the non-dispensing position is prevented, wherein the distance between the connector and the ferrule in the non-dispensing position of the valve is configured such that movement of the valve stem beyond the locking position is prevented during pressure-filling.

The present disclosure provides in another aspect a pressure-filling apparatus for a valve, comprising:

a source of pressurised fluid;

a nozzle for ejecting pressurised fluid from the source of pressurised fluid; and an engagement mechanism for coupling the nozzle to a connector provided on a valve stem of the valve.

The engagement mechanism may comprise jaws movable between a clamped position and an unclamped position.

Advantageously, the pressure-filling apparatus and the connector of the valve stem of the valve are adapted, each to the other, to ensure that the valve does not become inadvertently locked during pressure-filling. Advantageously, the pressure-filling apparatus allows for the automated and simple filling of the valve described above.

The jaws may be configured for clamping a connector in the form of a groove in the valve stem. Alternatively, the jaws may be configured for clamping a connector in the form of a flange on the valve stem.

The engagement mechanism may further comprise a leading face and the jaws are located behind the leading face.

The present disclosure provides in a further aspect, a valve comprising a valve body at least partially defining a fluid chamber for containing a fluid; and a valve stem extending into the fluid chamber, the valve stem comprising an outlet port;

wherein an external portion of the valve stem comprises a connector configured for connecting a pressure-filling apparatus to the valve.

The connector may be a groove in the external portion of the valve stem. Alternatively, the connector may be a flange on the external portion of the valve stem.

The present disclosure provides in a further aspect, a propellant dispenser comprising a container of propellant, wherein the container or propellant has a valved outlet that is moveable between a closed position, where propellant cannot exit the container, and an open position, where propellant can exit the container; the propellant dispenser additionally comprising a latching mechanism or other similar arrangement that prevents the valved outlet moving back to the closed position once moved to the open position.

Preferably, once the valved outlet has been moved to the open position, the entire volume of propellant in the container of propellant is discharged through the valved outlet. The container of propellant may be configured to contain a predetermined volume of propellant sufficient for the delivery of a dose of medicament.

The seal member of the valve of the present disclosure may be formed from any suitable material having acceptable performance characteristics. Preferred examples include nitrile, EPDM and other thermoplastic elastomers, butyl and neoprene.

Rigid components of the valve, such as the valve body, and valve stem may be formed, for example, from polyester, nylon, acetal or similar. Alternative materials for the rigid components of the valve may include stainless steel, ceramics and glass.

The locking member of the valve may be formed from a plastic or metal material. Preferably, the material exhibits a degree of elasticity. Suitable materials may include but are not limited to nylon, acetal, polyester, and high density polyethylene.

The fluid to be discharged by the valve may be a volatile propellant which is in the gaseous phase at standard temperature and pressure conditions (25° C. and 1 atm). The propellant may be held under pressurised conditions within the valve prior to discharge in a liquefied form. Suitable propellants include hydrofluoroalkanes (HFAs). Examples thereof include HFA134a, HFA227, HFA422d, HFA123, HFA245fa and HFA507c.

DESCRIPTION OF THE DRAWINGS

Embodiments of the present disclosure will now be described, by way of example only, with reference to the accompanying drawings, in which.

DETAILED DESCRIPTION

Figure 1:
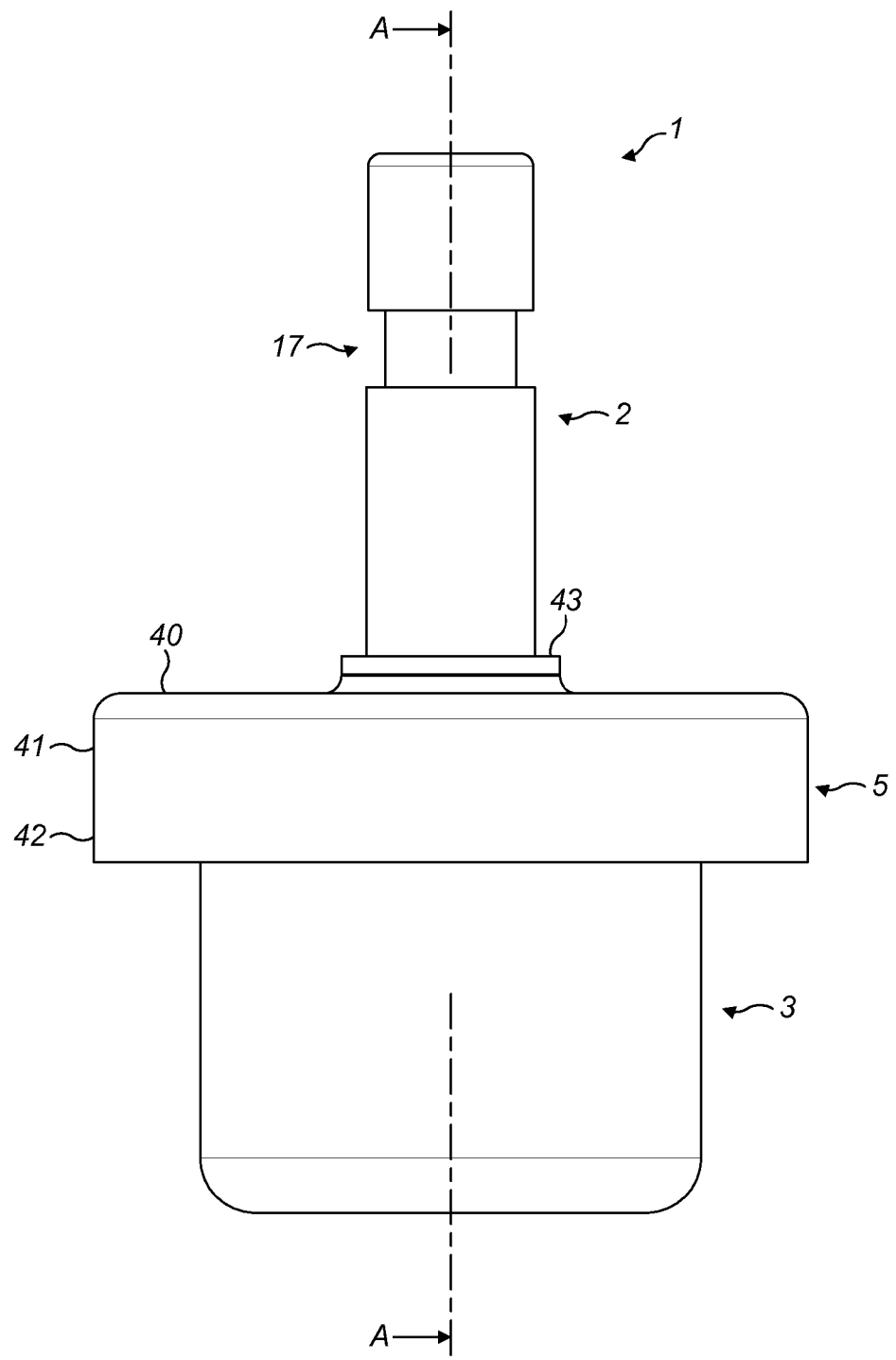
FIG. 1 is a side view of a first embodiment of valve according to the present disclosure.

A first embodiment of valve 1 in accordance with the present disclosure is illustrated in FIGS. 1 to 6. The valve 1 comprises a valve stem 2, a valve body 3, a compression spring 4, a ferrule 5, a seal member 6 and a locking member 7.

Figure 2:
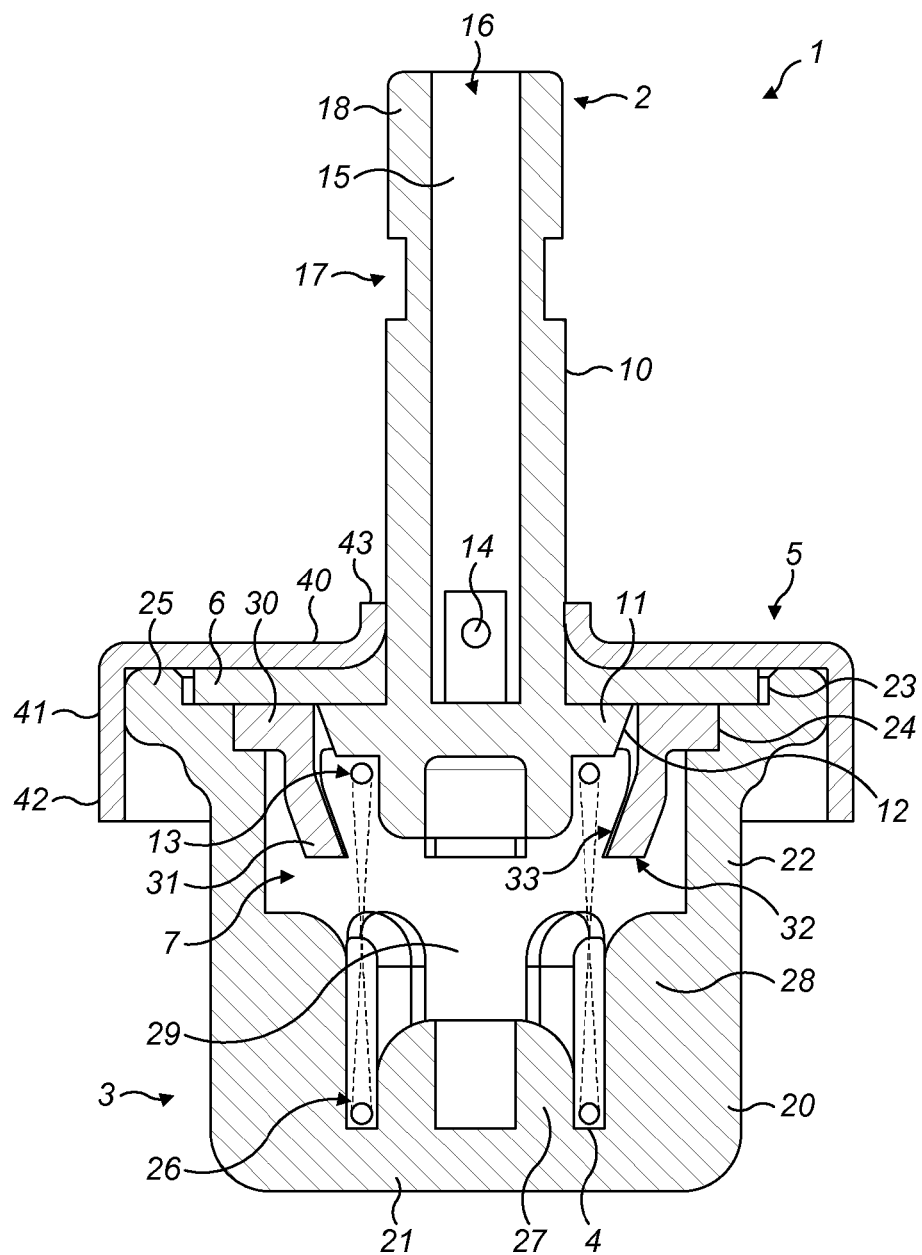
FIG. 2 is a cross-sectional view of the valve of FIG. 1 taken on section A-A, with a valve stem of the valve in a non-dispensing position.

In the following description of the valve 1 the relative terms "upper" and "lower", "up" and "down" and "above" and "below" and their derivatives are made with reference to the orientation of the valve 1 as shown in FIG. 2. However, it will readily be understood that the valve 1 may adopt, and be used in, any orientation.

Figure 7:
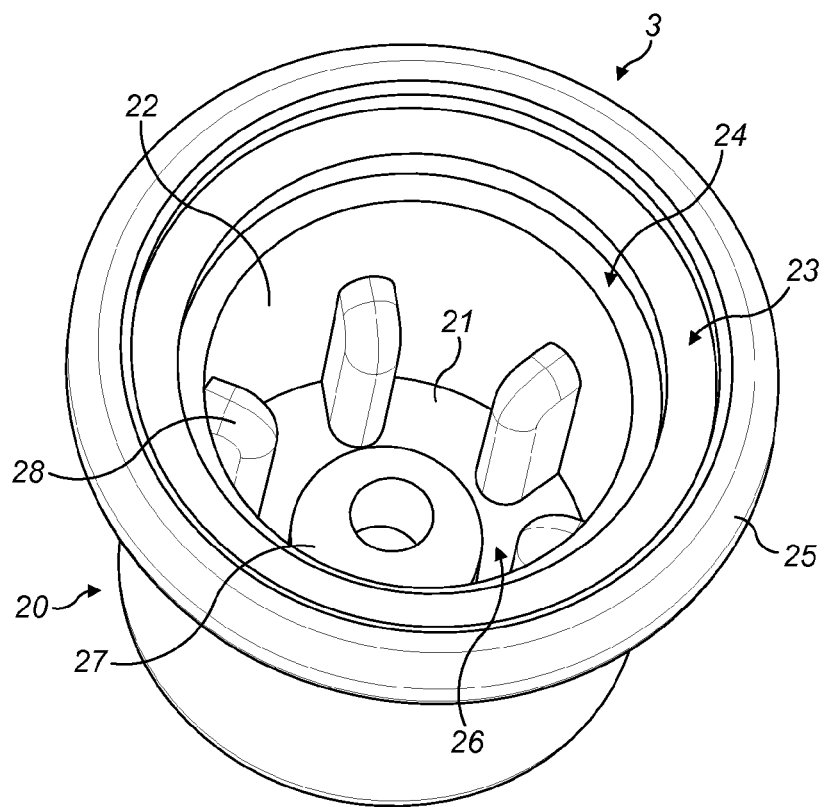
FIG. 7 is a perspective view of a valve body of the valve of FIG. 2.

As shown in FIGS. 2 and 7, the valve body 3 comprises a cup-shaped container 20 having a lower wall 21 and an annular side wall 22 which is open at an upper end opposite to the lower wall 21 for receiving the valve stem 2. An upper end of the annular side wall 22 is provided with a peripheral rim 25. A first recess 23 is formed near the peripheral rim 25 to define a seat for the seal member 6. A second recess 24 is provided adjacent and immediately below the first recess 23. The second recess 24 has a smaller diameter than the first recess 23 such that an internal face of the annular side wall 22 has a stepped profile. The second recess 24 defines a seat for the locking member 7. The valve body 3 is provided with a plurality of ribs 28. The ribs 28 project inwardly from the internal face of the annular side wall 22 and extend axially upwards from the lower wall 21 to a point approximately half way along the length of the cup-shaped container 20. As illustrated, six ribs 28 are provided equi-spaced around the circumference of the cup-shaped container 20. A centrally located annular extension 27 extends upwardly from an inner face of the lower wall 21 to define an annular zone between the centrally located annular extension 27 and the ribs 28. The annular zone defines a lower seat 26 for the compression spring 4.

The valve stem 2 comprises an elongate body 10 which is closed at a lower end by a flange 11 which extends across the elongate body 10 and extends outwardly thereof terminating in a tapered outer edge 12. A lower face of the flange 11 defines an upper spring seat 13. An upper end 18 of the elongate body 10 is open to form an outlet 16. An outlet port 14 is formed in the elongate body 10 a short distance above the position of the flange 11. The outlet port 14 provides for fluid communication between an exterior of the valve stem 2 and an internal bore 15 formed within the valve stem 2. An annular groove 17 is provided on an external portion of the valve stem 2 towards the upper end 18. The valve stem 2 may be formed as a unitary piece. Alternatively, if desired, for example to simplify assembly, the valve stem 2 may be formed from two or more pieces which are joined together to form the valve stem 2.

The seal member 6 is annular in shape with a central aperture sized to provide a dynamic, sliding seal with the exterior surface of the elongate body 10 of the valve stem 2. The seal member 6 may be formed from a thermoplastic elastomer, for example EPDM.

The compression spring 4 may be a helical spring. The compression spring 4 may have a spring rate of 0.4 to 1.2 N/mm. In one example the spring rate is 0.50 N/mm. In another example the spring rate is 1.0 N/mm.

The ferrule 5 comprises an annular metal component comprising a central aperture 43, a leading face 40 and a dependent side wall 41 which extends downwardly to terminate in a crimpable section 42.

Figure 6:
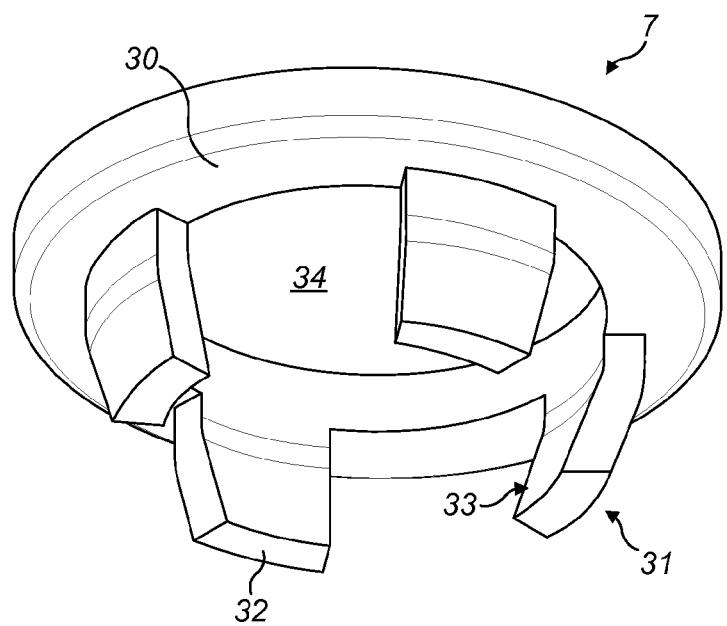
FIG. 6 is a perspective view of a locking member of the valve of FIG. 2.

As shown in FIGS. 2 and 6, the locking member 7 comprises an annular ring 30 having a central bore 34 and a plurality of latches 31 which depend therefrom. The annular ring 30 is sized to be larger than the outer diameter of the flange 11 of the valve stem 2. In the illustrated example, four latches 31 are provided which are equi-spaced around the circumference of the annular ring 30. Each latch 31 extends downwardly from a lower face of the annular ring 30 to terminate in a distal end 32. Each latch 31 is angled so as to have an angled inner face 33 which, on assembly, faces the valve stem 2 and is configured to make contact with the tapered outer edge 12 of the flange 11 of the valve stem 2 during use, as will be described further below.

The valve 1 is assembled by first inserting the compression spring 4 into the valve body 3 such that a lower end of the compression spring 4 is received in the lower seat 26. Separately, the seal member 6 is slid onto the valve stem 2 and located to be in contact with the upper face of the flange 11. Next, the locking member 7 is inserted into the cup-shaped container 20 so that the annular ring 30 rests in the second recess 24. The sub-assembly of the valve stem 2 and seal member 6 is then inserted such that the lower end and flange 11 of the valve stem 2 pass through the central bore 34 of the locking member 7 and the seal member 6 is engaged in the first recess 23. Finally, the ferrule 5 is engaged over the valve stem 2 with the elongate body 10 of the valve stem 2 projecting through the central aperture 43. The leading face 40 of the ferrule extends over and covers the seal member 6 and peripheral rim 25. The side wall 41 of the ferrule 5 extends downwardly around the peripheral rim 25. The crimpable section 42 is then crimped into the undercut formed on the external surface of the cup-shaped container 20 below the peripheral rim 25. (It should be noted that in the Figures for the sake of clarity, the ferrule 5 is shown un-crimped). The crimped ferrule 5 acts to retain the components of the valve 1 together and to apply a compressive force to the seal member 6.

On assembly, a fluid chamber 29 is delimited by the combination of the cup-shaped container 20 of the valve body 3 and the boundary formed by the seal member 6 and the valve stem 2. Thus, a container of propellant having a valved outlet is provided. In use, a fluid, such as a liquefied, volatile propellant, is held in the fluid chamber 29. In the illustrated example, the fluid chamber 29 is closed such that all fluid to be discharged in use is held within the fluid chamber 29 delimited by the valve body 3, the seal member 6 and the valve stem 2.

Once assembled, the compression spring 4 is partially compressed and extends between the lower seat 26 of the valve body 3 and the upper spring seat 13 of the valve stem 2 to bias the valve stem 2 into a non-dispensing position as shown in FIG. 2 in which the flange 11 is held in contact with the seal member 6. In the non-dispensing position the outlet port 14 is positioned above, or within the confines of, the seal member 6 such that there is no fluid communication path between the internal bore 15 of the valve stem 2 and the fluid chamber 29. Consequently, the fluid chamber 29 is sealed.

Figure 3:
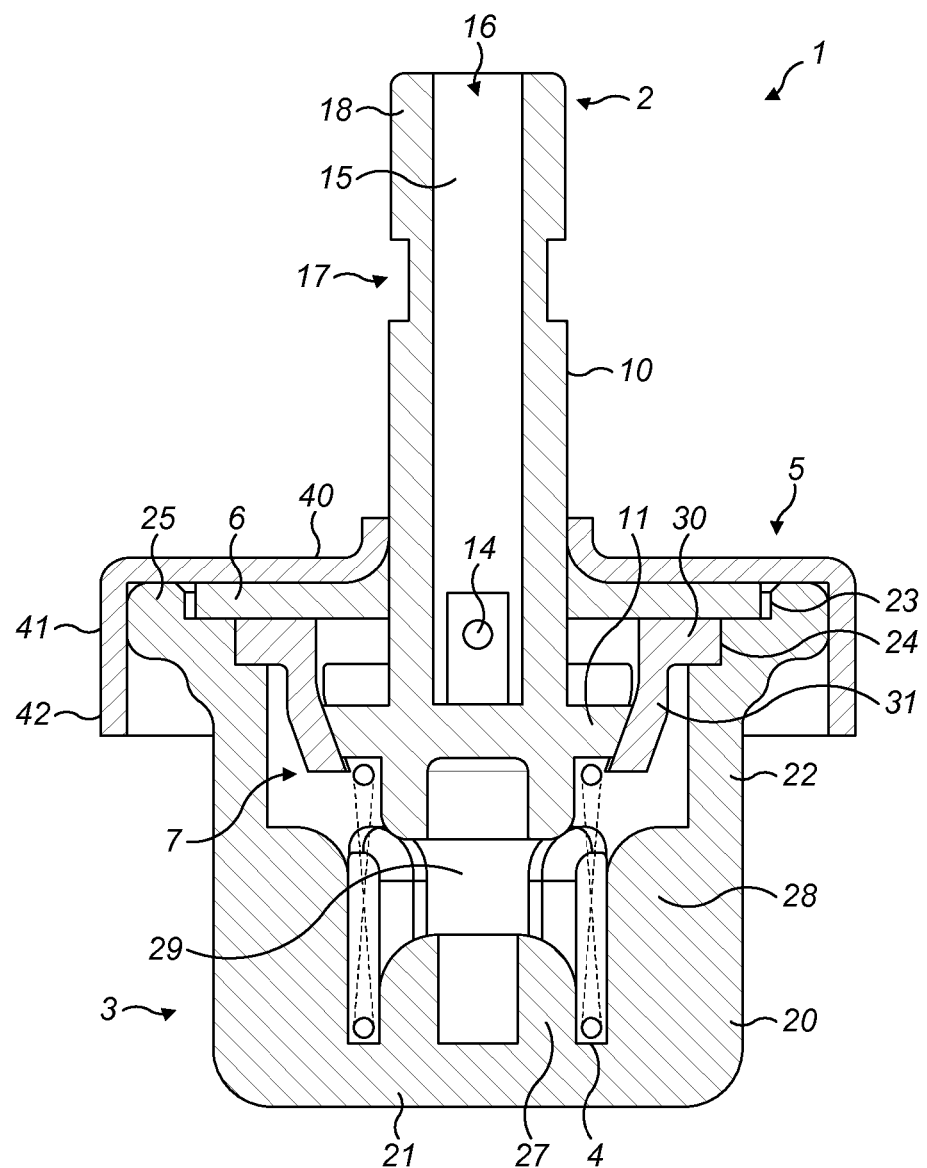
FIG. 3 shows the valve of FIG. 2 with the valve stem in an intermediate position.

FIGS. 2 to 5 illustrate operation of the valve 1. As noted above, FIG. 2 illustrates the non-dispensing position of the valve 1 when the valve 1 is at rest. FIG. 3 illustrates a position where the valve stem 2 has been depressed downwards a short distance. At this point, the tapered outer edge 12 has contacted the angled inner faces 33 of the latches 31 and has started to flex the latches 31 outwardly. The inter-engagement between the tapered outer edge 12 of the flange 11 and the angled inner faces 33 of the latches 31 is such as to relatively easily permit downward movement of the valve stem 2 relative to the locking member 7. In other words, the angling of the inter-engaging faces is such as to promote outward flexing of the latches 31 to permit passage therethrough of the flange 11.

Figure 4:
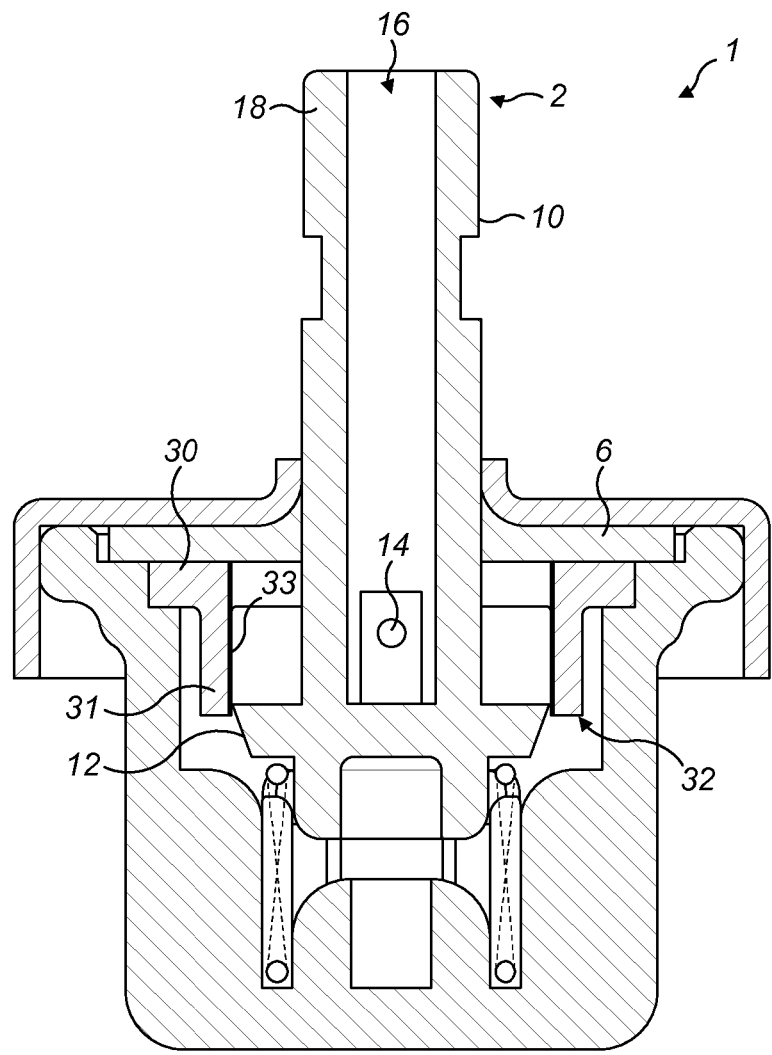
FIG. 4 shows the valve of FIG. 2 with the valve stem in further depressed beyond the intermediate position and just prior to reaching a locked position.

FIG. 4 illustrates the operating position where the flange 11 of the valve stem 2 is just about to move beyond the distal ends 32 of the latches 31. In this position as shown, the outlet port 14 of the valve stem 2 is in communication with the fluid chamber 29. This configuration of the valve 1 permits pressure-filling of the valve 1 as will be described further below.

Figure 5:
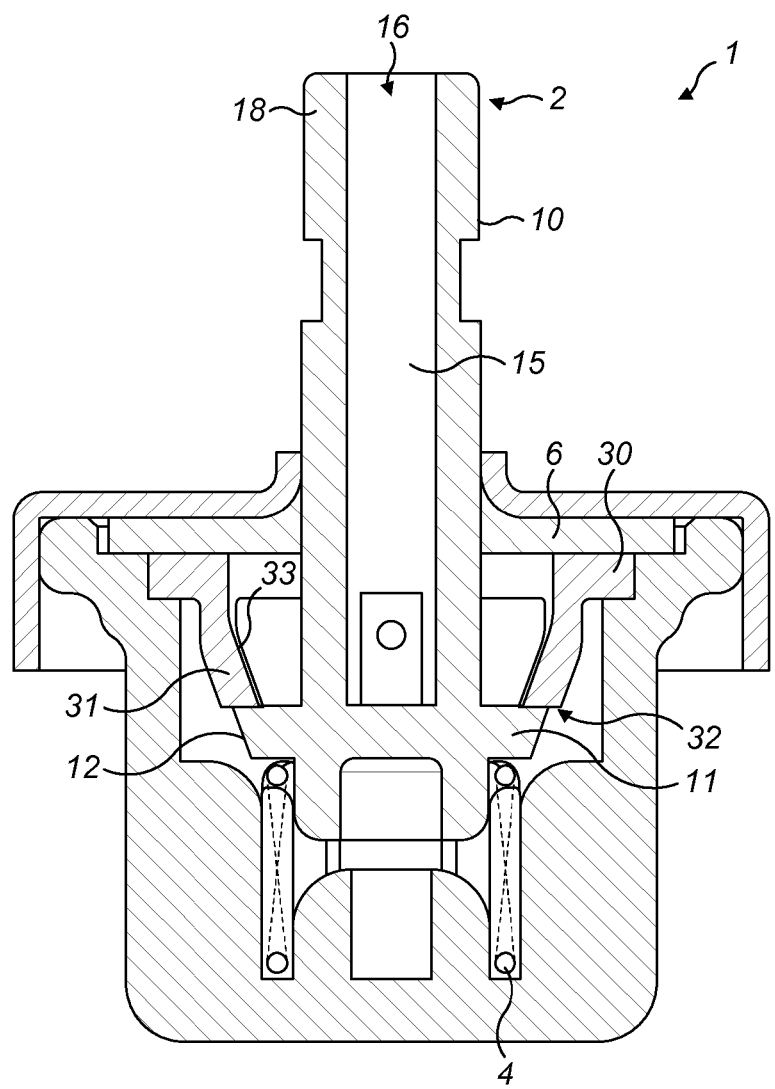
FIG. 5 shows the valve of FIG. 2 with the valve stem in the locked position.

FIG. 5 illustrates the position of the valve 1 when the valve 1 has become locked since the valve stem 2 has been further depressed downwards such that the flange 11 has moved beyond the locking member 7 and in particular because the tapered outer edge 12 of the flange 11 has become disengaged from the angled inner faces 33 of the latches 31. On such disengagement, the latches 31 spring back into their previous shape due to the elastic nature of the material of the locking member 7. Once this point has been reached, return of the valve stem 2 upwards into the non-dispensing position of FIG. 2 is prevented by inter-engagement between the upper face of the flange 11 with the distal ends 32 of the latches 31. In particular, since the surfaces of the flange 11 and latches 31 which are now in contact are not favourably tapered, each to the other, passage of the valve stem 2 back past the latches 31 is prevented. Thus, once locked in the dispensing position, the valve 1 remains in the dispensing position ensuring all of the fluid, such as volatile propellant, contained in the fluid chamber 29 is discharged via the outlet port 14, internal bore 15 and outlet 16.

As noted above, it is possible to position the valve stem 2 in a configuration, such as that shown in FIG. 4, where the valve stem 2 has not yet become locked but the outlet port 14 is in fluid communication with the fluid chamber 29. However, in practice (other than when pressure-filling the valve 1 as described below), operation of the valve 1 can be configured to ensure that movement of the valve stem 2 from the non-dispensing position of FIG. 2 to the locked, dispensing position of FIG. 5 will be achieved in a single, rapid, stroke that will not be stopped at the intermediate position of FIG. 4. For example, this may be achieved by configuring the valve stem 2 or ancillary components connected to the valve stem 2 to require a sufficient impulse to be applied to initiate movement of the valve stem 2. The impulse thus applied to the valve stem 2 acts to rapidly 'shoot through' the valve stem 2 into the locked position of FIG. 5.

Figure 8:
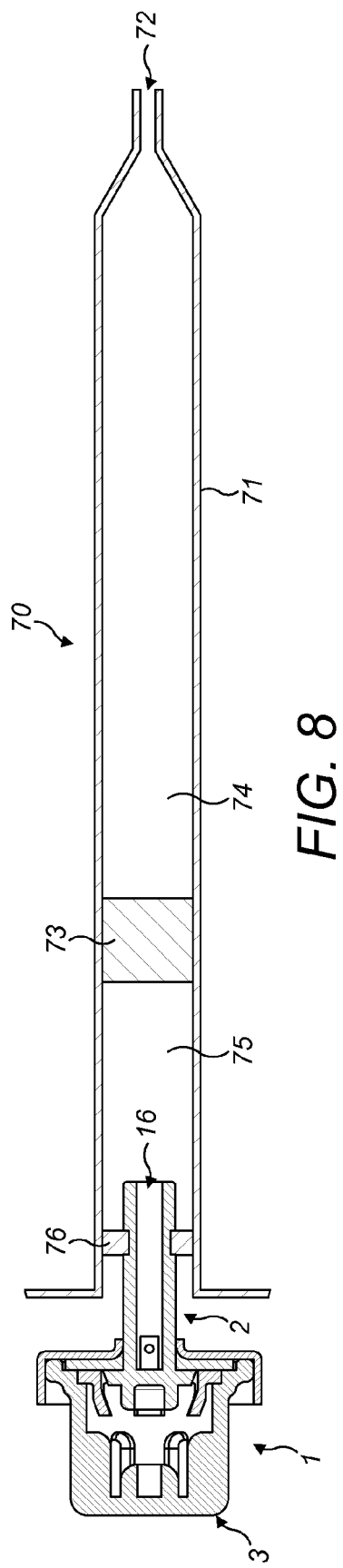
FIG. 8 schematically shows the valve of FIG. 2 assembled as part of a medicament syringe.

The valve 1 of the present disclosure may be utilised in many ways. One particular use of the valve 1 is as a means of providing a power source for actuating another device. FIG. 8 illustrates schematically one such scenario where the valve 1 contains a liquefied volatile propellant in fluid chamber 29 and is used as a power source for actuating a syringe 70. Other delivery devices or systems may be powered by the valve 1. The syringe 70 comprises a barrel 71 having an outlet 72 at one end which, in use, may be connected to a needle. An opposite end of the barrel 71 is open and receives the valve stem 2 of the valve 1. The valve stem 2 is mounted in sealing engagement with the syringe 70 by means of coupling ring 76 which engages in the groove 17 of the valve stem 2. The coupling ring 76 may also function as a fluid-tight seal. Alternatively, an additional fluid seal, such as an o-ring, may be provided extending between the valve stem 2 and the barrel 71. The fluid seal may be provided ahead or behind the location of the groove 17. The syringe 70 contains a stopper 73 which defines, within the barrel 71, a first chamber 74 ahead of the stopper 73 which is in communication with the outlet 72 and a second chamber 75 behind the stopper 73 with which the outlet 16 of the valve stem 2 communicates.

Figure 12:
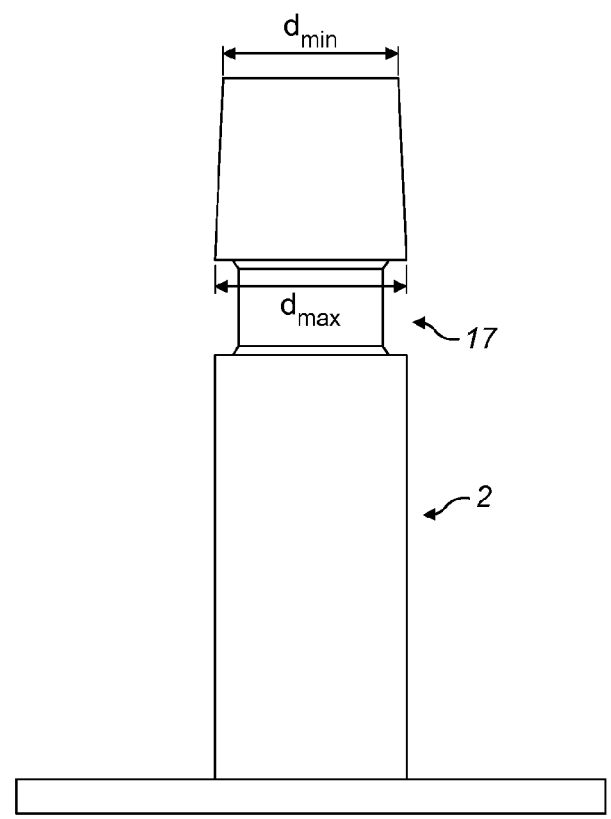
FIG. 12 shows an end portion of a valve stem for use in the valves of the present disclosure.

The valve stem 2 may have a tapered distal end as shown in FIG. 12. The portion of the valve stem 2 above the groove 17 may be tapered so as to narrow from an external diameter of $d_{max}$ immediately above the groove 17 to a diameter of $d_{min}$ at the distal end. Preferably the valve stem 2 may be tapered in this portion at an angle less than 6° inclusive, although a greater angle of taper may be of use. The taper of the valve stem 2 assist with coupling of the valve stem 2 with an external device, such as the syringe 70 shown in FIG. 8. In particular, the taper may assist in forming a fluid-tight seal where the valve stem 2 is inserted through an apertured sealing means such as a seal member, for example an o-ring.

In use, the first chamber 74 contains a fluid to be dispensed such as a liquid medicament. The second chamber 75 may contain a gas such as air at atmospheric pressure. To actuate the syringe 70, the valve body 3 of the valve 1 is depressed relative to the barrel 71 which causes depression of the valve stem 2 into its locked position as shown in FIG. 5. In this position, the liquefied volatile propellant in fluid chamber 29 rapidly boils off and the resultant gaseous propellant is discharged out of outlet 16 into the second chamber 75. This discharge may also displace propellant into the second chamber 75 that is still in the liquid phase. In this case, this liquid propellant continues to boil off into the gaseous phase within the second chamber 75. The resultant increase in the pressure within the second chamber 75 acts on the stopper 73 and propels it forwards towards the outlet 72, thus dispensing the liquid medicament out of the syringe 70.

It will be appreciated that the arrangement of FIG. 8 is schematic only, to show the principles of operation. In practice, additional features may be present. For example, a housing may be provided for securely coupling the valve 1 to the barrel 71; an actuator button may be provided which acts on the valve body 3 rather than the valve body 3 being directly contacted by the user's finger; etc.

Figure 10:
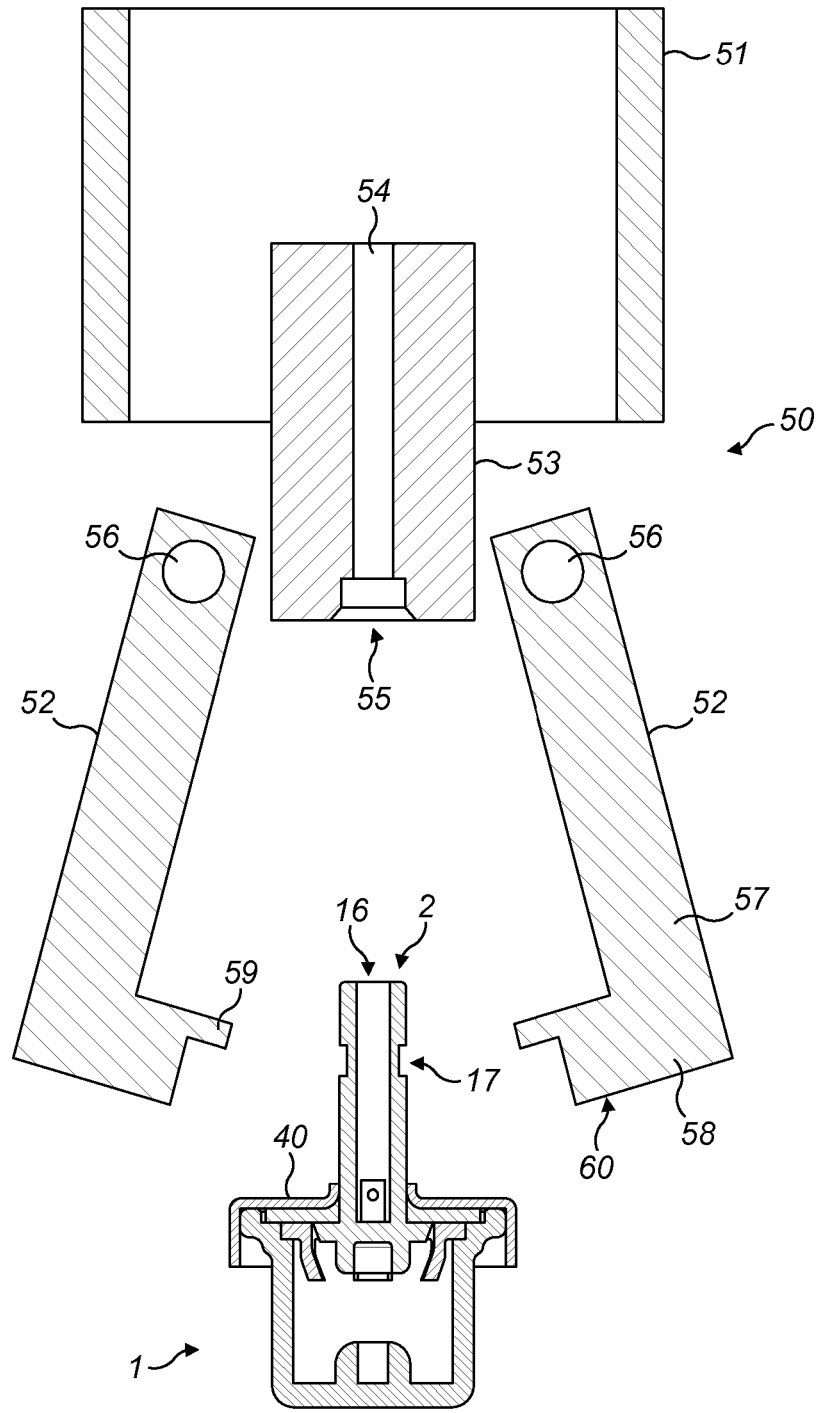
FIG. 10 schematically shows a pressure-filling apparatus for use with the valves of FIGS. 2 and 9.
Figure 11B:
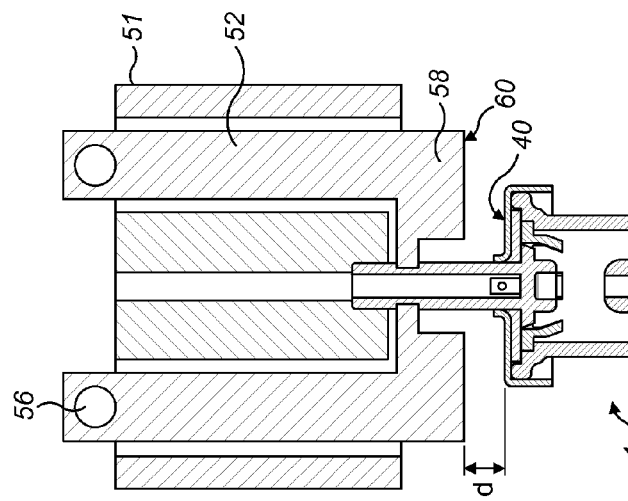
FIGS. 11a to 11c illustrated stages in the use of the pressure-filling apparatus of FIG. 10.
Figure 11A:
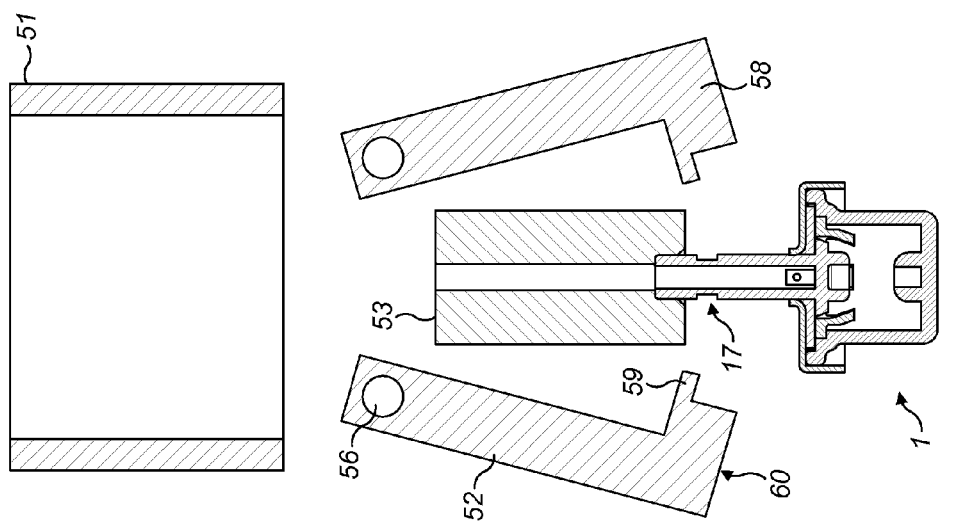
Figure 11C:
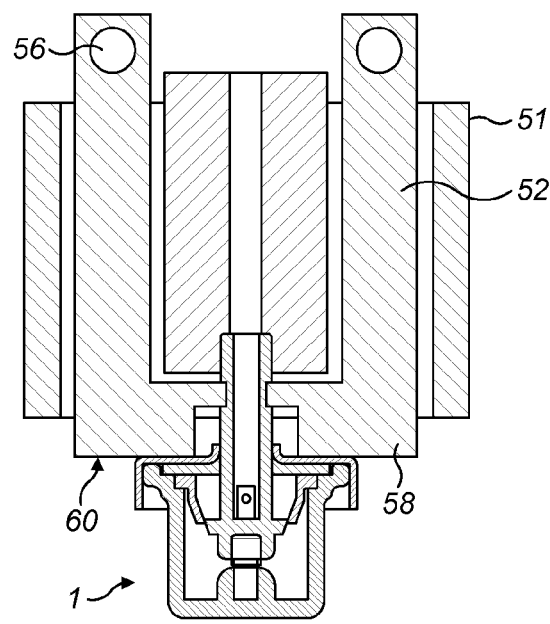

FIGS. 10 to 11c illustrate a pressure-filling apparatus 50 and method for pressure-filling the valve 1 with a fluid. The pressure-filling apparatus 50 is provided to permit pressure-filling of the fluid chamber 29 without locking the valve stem 2. The pressure-filling apparatus 50 comprises a nozzle 53 having an outlet end 55 shaped and configured to be able to sealingly engage with the outlet 16 of the valve stem 2 of the valve 1. The nozzle 53 is further provided with a supply conduit 54 connecting the outlet end 55 to a bulk supply of pressurised fluid (not shown). The pressure-filling apparatus 50 further comprises a pair of jaws 52. Each jaw 52 is pivotable about a pivot 56 at its upper end. Each jaw 52 comprises an elongate leg 57 extending downwardly from the pivot 56 and terminating in a foot 58 which extends perpendicularly from the elongate leg 57. The foot 58 of each jaw 52 comprises a toe 59 at an upper portion of the foot 58 which extends further away from the elongate leg 57 relative to the remainder of the foot 58. A lowermost face 60 of each foot 58 is thus spaced from the toe 59. The filling apparatus further comprises a collar 51 which may be cylindrical. It will be appreciated that the illustration of the pressure-filling apparatus 50 is schematic in nature and other components would in practice be present, to, for example, mount the jaws 52, collar 51 and nozzle 53 and to retain and manipulate the valve 1. These have been omitted from the Figures for clarity.

FIG. 10 illustrates the filling apparatus in an unengaged configuration with a valve 1 requiring pressure-filling. At this point, the valve 1 is in the non-dispensing position shown in FIG. 2. To pressure-fill the valve 1, the outlet 16 of the valve stem 2 is engaged with the outlet end 55 of the nozzle 53 as shown in FIG. 11a.

In the next stage as shown in FIG. 11b, the Collar 51 is moved downwards so as to engage and slide over the exterior of the jaws 52. Engagement between the collar 51 and jaws 52 causes the jaws 52 to pivot inwards about pivots 56 such that the toe 59 of each jaw 52 engages in the annular groove 17 of the valve stem 2. Proper engagement of the toe 59 in the annular groove 17 is ensured by pre-configuring the shape and size of the outlet end 55 of the nozzle 53 and the relative size and spacing of the jaws 52 and toe 59 to the location and position of the annular groove 17 of the valve stem 2 at the outlet 16. Thus, reliable engagement of the toes 59 in the annular groove 17 can be achieved simply by engaging the distal end of the valve stem 2 in the outlet end 55 of the nozzle 53.

In the intermediate position of FIG. 11b, it will be noted that the lowermost face 60 of each foot 58 is spaced by a distance 'd' from the leading face 40 of the ferrule 5 of the valve 1.

In the next stage, the collar 51 is moved further down causing it to inter-engage with the jaws 52 and to displace the jaws 52 downwards relative to the valve 1. The collar 51 may be provided with a lip (not shown) which engages with the jaws 52 and nozzle 53 to move them downwards. The jaws 52 are moved downwards by the distance 'd' until the lowermost face 60 of each foot 58 contacts the leading face 40 of the ferrule 5. At this point as shown in FIG. 11c, the metering valve 1 has been moved into the filling position of FIG. 4 wherein the outlet port 14 is in fluid communication with the fluid chamber 29 but the flange 11 has not been moved fully out of engagement with the latches 31 of the locking member 7. Further downward movement of the valve stem 2, which would cause the flange 11 of the valve stem 2 to move beyond the distal ends 32 of the latches 31 (and thus lock the valve stem 2 in the dispensing position), is prevented by inter-engagement between the lowermost face 60 of each foot 58 and the leading face 40 of the ferrule 5.

Pressure-filling of the fluid chamber 29 can now be carried out by discharging fluid through the supply conduit 54 of the nozzle 53 and through the internal bore 15 of the valve stem 2 and into the fluid chamber 29 via the outlet port 14. To complete the pressure-filling, the collar 51 and jaws 52 are moved back upwards to move the valve stem 2 into the non-dispensing position to seal off the outlet port 14 from the fluid chamber 29 by means of the seal member 6.

Figure 9:
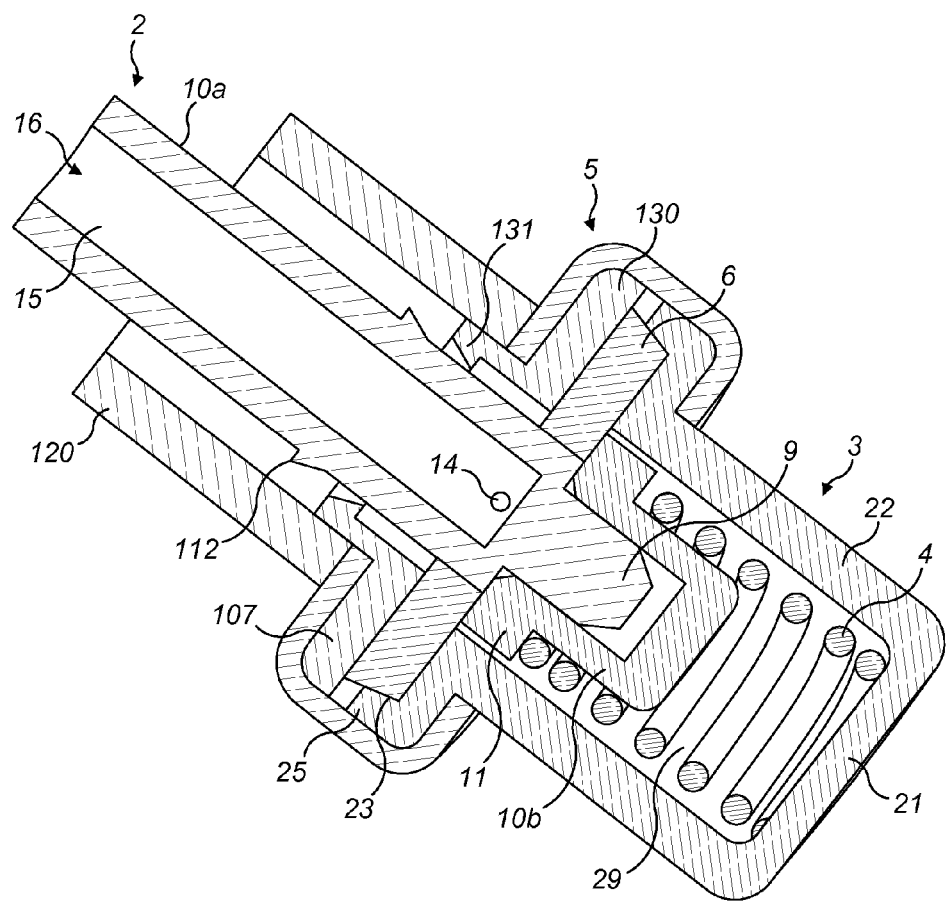
FIG. 9 shows a second embodiment of valve in accordance with the present disclosure in a non-dispensing position.

FIG. 9 illustrates a second embodiment of valve 1 in accordance with the present disclosure. Like components to the first embodiment have been referenced using like reference numerals. In the following, only the differences between the first and second embodiments will be discussed. in other respects, the construction, features and utilisation of the valve 1 are as described above with respect to the first embodiment.

The valve 1 of FIG. 9 differs in a number of respects.

Firstly, the valve body 3 comprises only a first recess 23 which defines a seat for the seal member 6.

Further, the valve stem 2 is formed from two pieces: a stem part 10a and a socket part 10b. The socket part 10b comprises the flange 11 and a cavity which receives a plug 9 formed at a lower end of the stem part 10a. The stem part 10a comprises the outlet port 14 but also a continuous ring 112 on its external surface. The ring 112 is provided with a tapered face which faces downwards. Instead of a continuous ring 112 a plurality of locking barbs may be provided.

The locking member 107 is located outside the fluid chamber 29 and is formed by a separate component that lies above and adjacent the seal member 6. The locking member 107 comprises an annular ring 130 and a set of upstanding legs which each terminate in a latch 131 which is inward-facing.

An external collar 120 may overlie the valve stem 2 and upstanding legs of the locking member 107 before use of the valve. The external collar 120 functions to prevent radially outward movement of the upstanding legs and thus movement of the valve stem 2 into the locked position. Prior to use the external collar 120 would be removed.

The ferrule 5 is crimped to retain the locking member 107, seal member 6 and valve body 3 together.

In use, pressure-filling and operation of the valve 2 is carried out as described above, except that the method of locking the valve in the dispensing position differs. In the second embodiment, the valve stem 2 becomes locked when the ring 112 of the valve stem 2 is moved beyond the location of the latches 131. The mutually-facing sloped faces of the latches 131 and the ring 112 that inter-engage on downward movement of the valve stem 2 permit passage of the ring 112 past the latches 131 on downward movement of the valve stem 2. However, the face of the ring 112 and the latches 131 that contact one another when the valve stem 2 then tries to move back upwards prevents return of the valve stem 2 into the non-dispensing position.

The invention claimed is:

1. A valve for discharging a fluid, comprising:
   a valve body at least partially defining a fluid chamber; and
   a valve stem extending into the fluid chamber, the valve stem comprising an outlet port for transfer, in use, of fluid from the fluid chamber into the valve stem;
   the valve stem being slidably movable relative to the valve body from:
   i) a non-dispensing position in which the outlet port is out of communication with the fluid chamber; to
   ii) a dispensing position in which the outlet port is in fluid communication with the fluid chamber so as to permit transfer of the fluid from the fluid chamber into the valve stem;

wherein the valve further comprises a locking member which is configured to irreversibly prevent return of the valve stem into the non-dispensing position once the valve stem slides beyond a locking position.

2. The valve of claim 1, wherein the valve is a single-discharge valve which is configured only to discharge a single quantum of fluid in a single discharge operation during its useful life.

3. The valve of claim 1, wherein the locking member is located within the valve body.

4. The valve of claim 1, wherein the locking member is formed as a part of the valve body.

5. The valve of claim 1, wherein the locking member is located outside the valve body.

6. The valve of claim 1, wherein the locking member and the valve stem comprise inter-engaging members, wherein the inter-engaging members:
   a) contact one another during movement of the valve stem towards the dispensing position and permit movement of the valve stem into the dispensing position; and
   b) contact one another during attempted movement of the valve stem from beyond the locking position back towards the dispensing position and prevent movement of the valve stem back into the non-dispensing position.

7. The valve of claim 6, wherein the inter-engaging members contact one another during movement of the valve stem towards the dispensing position and permit movement of the valve stem into the dispensing position by flexing or other distortion of at least one of the inter-engaging members.

8. The valve of claim 6, wherein the inter-engaging member of the valve stem comprises a flange.

9. The valve of claim 8, wherein a distal edge of the flange is angled to promote flexing of the locking member during movement of the valve stem into the dispensing position.

10. The valve of claim 6, wherein the locking position of the valve stem is defined as a point where the inter-engaging member of the valve stem slides beyond, and disengages from, the inter-engaging member of the locking member.

11. The valve of any of claim 6, wherein the inter-engaging member of the locking member comprises at least one flexible latch.

12. The valve of claim 11, wherein the at least one flexible latch exhibits elastic behaviour.

13. The valve of claim 11, wherein the locking member comprises four flexible latches.

14. The valve of claim 13, wherein the locking member comprises an annular ring and the four flexible latches are equi-spaced about the annular ring.

15. The valve of claim 1, wherein the valve further comprises a biasing member for biasing the valve stem into the non-dispensing position.

16. The valve of claim 15, wherein the biasing member is a compression spring located in the valve body and extending between the valve body and the valve stem.

17. The valve of claim 1, wherein the valve further comprises a seal member sealing between the valve body and the valve stem.

18. The valve of claim 17, wherein the valve body comprises a cup-shaped portion having an open mouth through which extends the valve stem; wherein the open mouth is closed by the seal member.

19. The valve of claim 17, wherein the valve further comprises a crimped ferrule for retaining the seal member in sealing engagement with the valve body and valve stem.

20. The valve of claim 17, wherein the valve comprises only a single seal member in the form of the seal member which functions as both a dynamic seal with the valve stem and a static seal with the valve body.

21. The valve of claim 17, wherein the fluid chamber is closed by the valve body and the seal member such that, in use, a quantum of fluid is sealed within the fluid chamber.

22. The valve of claim 1, wherein prior to movement of the valve stem beyond the locking position, the valve stem is slidably movable relative to the valve body into:
   a filling position in which the outlet port is in fluid communication with the fluid chamber to allow pressure-filling of the fluid chamber via the valve stem and outlet port.

23. The valve of claim 1, wherein an external portion of the valve stem comprises a connector for releasably connecting the valve stem to a pressure-filling apparatus.

24. The valve of claim 23, wherein the connector is a groove in the valve stem.

25. The valve of claim 23, wherein the connector is a flange on the valve stem.

26. The valve of claim 1, wherein the valve stem comprises a tapered distal end.

27. A method of powering actuation of a medicament dispenser, comprising utilizing a valve as claimed in claim 1, which can only discharge a single quantum of volatile propellant fluid in a single discharge operation during its useful life, to power actuation of the medicament dispenser.

28. The method as claimed in claim 27, wherein the medicament dispenser is a syringe, an ophthalmic delivery device, a nasal system, an oral inhaler, or a transdermal delivery device.

29. The method as claimed in claim 27, wherein
   the fluid chamber of the valve is a propellant fluid chamber for containing a propellant fluid.

30. A syringe comprising:
   a barrel having an outlet at a front end; and
   a stopper axially movable in the barrel;
   the syringe further comprising a valve as claimed in claim 1.

31. A syringe as claimed in claim 30, wherein the valve in the non-dispensing position comprises a volatile propellant within the fluid chamber, wherein the syringe may be actuated to move the stopper in the barrel by moving the valve stem into the dispensing position.

32. A syringe as claimed in claim 30, wherein the stopper defines and separate a first chamber and a second chamber, the first chamber being axially forwards of the stopper and being configured for containing a medicament, and the second chamber being axially rearwards for the stopper and being configured to receive propellant from an outlet of the valve stem.

33. A syringe as claimed in claim 30, wherein the valve is coupled to a rear end of the barrel of the syringe.

34. A syringe as claimed in claim 30, further comprising a manually movable actuator for actuating the valve.

35. A syringe as claimed in claim 34, wherein the manually movable actuator is a button or flexible membrane coupled to the valve body of the valve.

36. A valve as claimed in claim 1,
   wherein an external portion of the valve stem comprises a connector configured for connecting a pressure-filling apparatus to the valve.

37. The valve of claim 36, wherein the connector is a groove in the external portion of the valve stem.

38. The valve of claim 36, wherein the connector is a flange on the external portion of the valve stem.

39. The valve of claim 36, wherein the valve stem comprises a tapered distal end.

40. A method of discharging a fluid from a valve of the type comprising:
  a valve body at least partially defining a fluid chamber containing a fluid; and
  a valve stem extending into the fluid chamber, the valve stem comprising an outlet port;
  the method comprising the steps of:
  i) starting with the valve stem in a non-dispensing position in which the outlet port is out of communication with the fluid chamber;
  ii) moving the valve stem by a sliding stroke relative to the valve body into a dispensing position in which the outlet port is in fluid communication with the fluid chamber to thereby transfer the fluid from the fluid chamber into the valve stem via the outlet port;
  iii) discharging the fluid from an external open end of the valve stem;
  wherein during the sliding stroke of step ii) the valve stem is locked by being moved beyond a locking position such that return of the valve stem into the non-dispensing position is irreversibly prevented and the valve stem is maintained in the discharging position to thereby ensure that the fluid contained in the fluid chamber is fully discharged.

41. The method of claim 40, wherein the valve can only discharge a single quantum of fluid in a single discharge operation during its useful life.

42. The method of claim 40, wherein return of the valve stem into the non-dispensing position from beyond the locking position is prevented by inter-engagement between the valve stem and a locking member.

43. The method of claim 42, wherein the inter-engagement between the valve stem and the locking member:
  a) produces contact therebetween during movement of the valve stem towards the dispensing position and permits movement of the valve stem into the dispensing position; and
  b) produces contact therebetween during attempted movement of the valve stem from beyond the locking position back towards the dispensing position and prevents movement of the valve stem back into the non-dispensing position.

44. The method of claim 42, wherein the valve stem and/or the locking member flex or otherwise distort as the valve stem moves beyond the locking position.

45. The method of claim 44, wherein the valve stem and/or the locking member flex or otherwise distort elastically as the valve stem moves beyond the locking position.

46. The method of claim 42, wherein the valve stem becomes locked at a point where a flange of the valve stem slides beyond, and disengages from, the locking member.

47. The method of claim 40, wherein the valve stem is biased into the non-dispensing position.

48. The method of claim 40, wherein the fluid chamber is closed by the valve body and a seal member such that, in use, a quantum of fluid is sealed within the fluid chamber.

49. The method of claim 40, wherein the fluid comprises a volatile propellant.

50. The method of claim 40, wherein prior to movement of the valve stem beyond the locking position, the valve stem is slidably movable relative to the valve body into:
  a filling position in which the outlet port is in fluid communication with the fluid chamber to allow pressure-filling of the fluid chamber via the valve stem and outlet port.

51. A method of pressure-filling a valve of the type comprising:
  a valve body at least partially defining a fluid chamber;
  a valve stem extending into the fluid chamber, the valve stem comprising an outlet port;
  a seal member sealing between the valve body and the valve stem; and
  a ferrule for retaining the seal member and valve stem to the valve body;
  wherein an external portion of the valve stem comprises a connector;
  the method comprising the steps of:
  i) starting with the valve stem in a non-dispensing position in which the outlet port is out of communication with the fluid chamber;
  ii) engaging a pressure-filling apparatus with the connector of the valve stem;
  iii) moving the valve stem into a filling position, by operation of the pressure-filling apparatus, such that the valve stem slides relative to the valve body until the pressure-filling apparatus contacts the ferrule;
  iv) pressure-filling the fluid chamber and/or valve body; and
  v) moving the valve stem, by operation of the pressure-filling apparatus, back into the non-dispensing position;
  wherein the distance between the connector and the ferrule in the non-dispensing position of the valve is configured such that in the filling position, with the pressure-filling apparatus in contact with the ferrule, the outlet port of the valve stem is in fluid communication with the fluid chamber to permit transfer of fluid into the fluid chamber;
  wherein the valve further comprises a locking member such that the valve stem can be locked in a dispensing position by being moved beyond a locking position such that return of the valve stem into the non-dispensing position is irreversibly prevented, wherein the distance between the connector and the ferrule in the non-dispensing position of the valve is configured such that movement of the valve stem beyond the locking position is prevented during pressure-filling.

52. A propellant dispenser comprising a container of propellant, wherein the container or propellant has a valved outlet that is moveable between a closed position, where propellant cannot exit the container, and an open position, where propellant can exit the container; the propellant dispenser additionally comprising a latching mechanism that irreversibly prevents the valved outlet moving back to the closed position once moved beyond a locking position.

53. The propellant dispenser of claim 52, wherein, once the valved outlet has been moved to the open position, the entire volume of propellant in the container of propellant is discharged through the valved outlet.

54. The propellant dispenser of claim 52, wherein the container of propellant is configured to contain a predetermined volume of propellant sufficient for the delivery of a dose of medicament.

* * * * *